ized by lowering the temperature of the mixture of fusogenic unilamellar lipid vesicles and integral membrane proteins to at or below the phase transition temperature of the fusogenic unilamellar lipid vesicles. A proteoliposome, a medicament comprising the proteoliposome and a drug or other biologically or physiologically active agent, and a method of treatment comprising administering the medicament to an afflicted host are also disclosed. The proteoliposomes are larger than conventional proteoliposomes and are more stable than conventional unilamellar lipid vesicles.

United States Patent [19]
Scotto et al.

[11] Patent Number: 4,873,089
[45] Date of Patent: Oct. 10, 1989

[54] PROTEOLIPOSOMES AS DRUG CARRIERS

[75] Inventors: Anthony W. Scotto, Middle Village; David Zakim, Armonk, both of N.Y.

[73] Assignee: Cornell Research Foundation Inc., Cornell University, Ithaca, N.Y.

[21] Appl. No.: 171,197

[22] Filed: Mar. 21, 1988

Related U.S. Application Data

[63] Continuation of Ser. No. 754,319, Jul. 12, 1985, abandoned.

[51] Int. Cl.$^4$ .............................................. A61K 37/22
[52] U.S. Cl. .................................................... 424/450
[58] Field of Search ................. 424/417, 450; 264/4.1, 264/4.3, 4.6; 428/402.2

[56] References Cited

U.S. PATENT DOCUMENTS 3,937,668  2/1976  Zolle ..................................... 264/4.3
4,560,665 12/1985  Nakae et al. ............................ 424/2

Primary Examiner—Douglas W. Robinson
Assistant Examiner—Raymond J. Henley
Attorney, Agent, or Firm—Sughrue, Mion, Zinn, Macpeak, and Seas

[57] ABSTRACT

A process for the preparation of proteoliposomes comprising: (1) mixing a fusogen with lipid components used to form unilamellar lipid vesicles to thereby form fusogenic unilamellar lipid vesicles; and (2) activating the fusogenic unilamellar lipid vesicles in the presence of integral membrane proteins to thereby form fusogenic proteoliposomes, wherein the fusogenic unilamellar lipid vesicles are activated by lowering the temperature of the mixture of fusogenic unilamellar lipid vesicles and integral membrane proteins to at or below the phase transition temperature of the fusogenic unilamellar lipid vesicles. A proteoliposome, a medicament comprising the proteoliposome and a drug or other biologically or physiologically active agent, and a method of treatment comprising administering the medicament to an afflicted host are also disclosed. The proteoliposomes are larger than conventional proteoliposomes and are more stable than conventional unilamellar lipid vesicles.

10 Claims, No Drawings

PROTEOLIPOSOMES AS DRUG CARRIERS

This is a continuation of application Ser. No. 754,319, filed July 12, 1985, now abandoned.

FIELD OF THE INVENTION

This invention relates to the preparation of unilamellar lipid vesicles containing integral membrane proteins firmly embedded in the lipid bilayer of the vesicles (hereinafter referred to as proteoliposomes). More specifically, the present invention relates to the inclusion of fusogens into unilamellar vesicles of phospholipids (hereinafter sometimes referred to as "ULVs") to create a ULV which is capable f fusion with integral membrane proteins, other fusogenic ULVs and fusogenic proteoliposomes. The fusion property of these vesicles can be controlled by the nature of the added fusogen and by temperature and can be controlled by changing the temperature. These proteoliposomes are stable and have usefulness as carriers of various compounds including drugs for in vivo administration.

BACKGROUND OF THE INVENTION

The use of ULVs as drug carriers has been the subject of extensive investigation. The lack of stability of lecithin liposomes in vivo and the toxicity of many of the lipid compounds added to increase stability in vivo have limited the usefulness of liposomes as carriers for administration of drugs. The proteoliposome is an alternative vehicle for these objectives.

Studies of the properties of proteins that are integral components of membranes depend on dissolution of the membrane with detergents, separation of the protein of interest from other membrane components, and finally re-introducing the protein into a matrix of phospholipid. The latter may have a variety of physical structures, depending on the complex of protein and phospholipid being studied. The complex of most interest, because of its resemblance to naturally occurring biological membranes, is reconstitution of integral membrane proteins into unilamellar bilayers of phospholipid. Protein-phospholipid structures of this form can be obtained in several different ways. As far as is known, the method for preparing these structures does not affect the properties of the protein or lipid, assuming the protein functions in a stable manner under the conditions used to reconstitute the protein-phospholipid vesicle.

The most popular techniques for achieving reconstitution of a protein-phospholipid vesicle include co-sonication of protein and phospholipid (Racker, E. (1973) *Biochem. Biophys. Res. Communs.* 55, 224–230; Carol, R. C. and Racker, E. (1977) *J. Biol. Chem.* 252, 6981–6990; Banerjee, R. K., Shertzer, H. G., Kanner, B. I. and Racker, R. (1977) *Biochem. Biophys. Res. Communs.* 75, 772–778) and slow dialysis of mixtures of integral membrane protein, phospholipid and detergent (Kagawa, Y. and Racker, E. (1971) *J. Biol. Chem.* 246, 5477–5487; Hinkle, R. C., Kim, J. J. and Racker, E. (1972) *J. Biol. Chem.* 247, 1338–1339; Racker, E. (1972) *J. Biol. Chem.* 247, 8198–8200; Kagawa, Y., Kandrach, A. and Racker, E. (1973) *J. Biol. Chem.* 248, 676–684). Direct insertion of selected small proteins, such as mellitin (Vogel, H. (1981) *FEBS. Lett.* 134, 37–42; Jahnig, F. (1983) *Proc. Nat'l Acad. Sci.* 80, 3691–3695; Vogel, H., Jahnig, F., Hoffman, V. and Stumpfel, J. (1983) *Biochem. Biophys. Acad.* 733, 201–209) or microsomal cytochrome $b_5$ (Enoch, H. G., Fleming, P. J. and Strittmatter, P. (1977) *J. Biol. Chem.* 252, 5656–5660) into preformed phospholipid vesicles apparently can be achieved. In a limited number of instances, the use of specific mixtures of phospholipids in the bilayer has led to direct and spontaneous incorporation into the bilayer of specific integral membrane proteins, as for example cytochrome oxidase (Eytan, G. D., Matheson, M. J. and Racker, E. (1976) *J. Biol. Chem.* 251, 6831–6837; Eytan, G. D. and Broza, R. (1978) *J. Biol. Chem.* 253, 3196–3202). Small proteins, such as mellitin, that insert spontaneously into vesicles appear to attach to the membrane by a single region of $\alpha$-helix and the driving force for insertion is believed to be a transition from the form of a random coil in water to that of an $\alpha$-helix in the bilayer (Jahnig, F. (1983) *Proc. Nat'l Acad. Sci.* 80, 3691–3695). The mechanism by which a protein such as cytochrome oxidase incorporates spontaneously into bilayers with limited specific composition is unclear.

The most generally useful method for reconstituting large integral membrane proteins, based on its popularity, is the formation of protein-lipid vesicles by slow dialysis of a mixture of protein, phospholipid and detergent. This and the method of co-sonication have been used almost exclusively as a means for studying the influence of the lipid millieu on the properties of the protein. These techniques have proved extremely valuable in this context. On the other hand, these commonly used techniques for reconstituting complexes of protein and lipid provide little information on the mechanism(s) by which integral membrane proteins in cells might enter biological membranes. Thus, although many proteins insert into intracellular membranes as they are translated on ribosomes attached to these membranes (Blobel and Doberstein (1975) *J. Cell. Biol.* 67, 835–851), it is clear that this is not so for all such proteins (Ross, E. and Schatz, G. (1976) *J. Biol. Chem.* 251, 1997–2004; Maccecchini, M. L., Rudin, Y., Blobel, G. and Schatz, G. (1979) *Proc. Nat'l Acad. Sci. U.S.A.* 76, 343–347; T., Goodman, J. M. and Wickner, W. (1980) *Proc. Nat'l Acad. Sci. U.S.A.* 77, 4669–4673).

SUMMARY OF THE INVENTION

Accordingly, one object of the present invention is to provide more stable large proteoliposomes capable of carrying drugs.

These and other objects of the present invention have been accomplished by providing a process for the preparation of proteoliposomes comprising: (1) mixing a fusogen with lipid components used to form unilamellar lipid vesicles to thereby form fusogenic unilamellar lipid vesicles; and (2) activating the fusogenic unilamellar lipid vesicles in the presence of integral membrane proteins to thereby form fusogenic proteoliposomes, wherein the fusogenic unilammelar lipid vesicles are activated by lowering the temperature of the mixture of fusogenic unilamellar lipid vesicles and integral membrane proteins to at o below the phase transition temperature of the fusogenic unilamellar lipid vesicles.

A proteoliposome, a medicament comprising the proteoliposome and a drug or other biologically or physiologically active agent, and a method of treatment comprising administering the medicament to an afflicted host are also disclosed.

DETAILED DESCRIPTION OF THE INVENTION

According to the present invention, ULVs which are capable of fusion are prepared. ULVs are made capable of fusion by the inclusion of certain lipophilic molecules into these vesicles during preparation of the vesicles. The lipophilic molecules which render the ULVs capable of fusion in response to temperature are designated fusogens. The property of a lipophilic molecule that categorizes it as a fusogen is the behavior of said molecule in the gel phase array of a phospholipid bilayer, as will be described later.

The mixing of integral membrane proteins with fusogenic unilamellar vesicles will result in incorporation of said proteins when conditions are manipulated to activate the fusogenic property of the ULV (unilamellar vesicles which contain a fusogen).

The fusion of the first fusogenic ULV with an integral membrane protein results in a fusogenic proteoliposome. Next, fusion of the proteoliposome with other fusogenic ULVs and with other fusogenic proteoliposomes occurs. The fusion of the proteoliposome with other fusogenic ULVs and with other fusogenic proteoliposomes is a property conferred by the fusogen and its concentration in the vesicle.

The manipulation of the fusogenic property of these fusogenic ULVs and proteolipsomes is regulated by temperature. ULVs are prepared above the phase transition of the phospholipid, that is, the lipids are in the liquid crystalline phase. In the absence of a fusogen, ULVs of phospholipids are stable and do not fuse with other vesicles or integral membrane proteins. The inclusion of a fusogen, however, results in fusogenic ULVs causing rapid fusion of integral membrane proteins with ULVs, fusion of fusogenic proteoliposomes with fusogenic ULVs, and fusion of fusogenic proteoliposomes with each other. The temperature for fusion depends on the nature of the fusogen, but in this invention, the temperature is at or below tne phase transition temperature of the fusogenic ULVs.

In the instance that different phospholipids do not form ideal mixtures, the phase transition temperature of the bulk of the phospholipids in a vesicle is not the only phase transition temperature that can be manipulated to cause fusogenic ULVs to fuse. "Clusters" of phospholipids which do not mix with the bulk of the phospholipids of the vesicle exhibit a phase transition temperature separate from that due to the "bulk" phospholipid, and this may also be used to cause fusion due to the presence of fusogens included in these clusters.

For information on the miscibility of phospholipids, reference can be made to Silius, J. R., "Thermotropic Phase Transition of Pure Lipid in Model Membranes and Their Modification by Membrane Proteins in: *Lipid-Protein Interactions*, Jost, P. C. and Griffith, O. H. (1982), John Wiley & Sons, New York, Vol. II, pp. 239-281.

The present invention also provides a fusogenic proteoliposome constructed from integral membranes proteins, fusogenic ULVs, and fusogenic proteoliposomes. The fusogenic ULVs comprise a mixture of phospholipid and a fusogen and the fusogenic proteoliposomes comprise a fusogenic ULV into which an integral membrane protein has been inserted, a fusogenic ULV fused with a fusogenic proteoliposome, or two or more fused fusogenic proteoliposomes. The fusogen present in the fusogenic ULV and the fusogenic proteoliposome must be present in an amount sufficient to cause continued fusion of the fusogenic ULVs and the fusogenic proteoliposome. However, a lower concentration of fusogen is required for fusion between a ULV and an integral membrane protein than for fusion between two ULVs.

The procedure described herein for preparing the proteoliposomes of this invention is unique in several ways. First, the preformed small ULVs are made capable of a temperature regulated fusion by the inclusion of a fusogen into the phospholipid bilayer of the vesicle. Second, these fusogenic ULVs can be formed in sizes ranging upward to several microns (0.1-10 microns) by allowing the fusion to proceed between fusogenic ULVs and fusogenic proteoliposomes and/or between two or more fusogenic proteoliposomes. Therefore, small ULVs that contain entrapped compounds including drugs and/or naturally occurring proteins and metabolic intermediates on the inside of the vesicle can be converted to large proteoliposomes. Third, the process of incorporating integral membrane proteins into these fusogenic unilamellar vesicles occurs under mild, non-denaturing conditions.

The initial phase of forming the proteoliposomes is an extremely rapid, complete insertion of all available integral membrane protein into fusogenic ULVs, followed by a somewhat slower increase in size and lipid-to-protein ratio of ULVs containing protein. As already stated, this allows fusogenic small ULVs to be converted into more stable proteoliposomes, which can be formed in sizes ranging upward to several microns (0.1 to 10 microns). The extent of secondary growth of the proteoliposomes can be limited by the availability of fusogenic ULVs in the mixture. Also, the process of growth can be stopped at any time by raising the temperature.

The integral membrane proteins appear to be inserted into ULVs with a uniform and predictable, not a random, orientation with regard to the inside and outside of the vesicle. However, the inventors do not want to be bound by this statement.

For preparing the fusogenic ULVs of the present invention, the lipids of the ULVs can be any phospholipid so long as a specific fusogen for that composition is included in the ULV.

Concerning the preparation of ULVs, reference can be made to Huang, C., "Studies in Phosphatidylcholine Vesicles: Formation and Physical Characteristics" (1969), *Biochemistry* 8, 344-352; Batzri, S., and Korn, E. D. (1973), *Biochem. Biophys. Acta* 298, 1015-1019; Reeves, J. P. and Dowben, R. M. (1970), *J. Memb. Biol.* 3, 123-141; Deamer, D. and Bangham, A. D. (1976), *Biochem. Biophys. Acta* 443, 629-634; Hamilton, R. L. and Guv, L. S. S., in *Liposome Technology*, Gregorirdis (ed.) CRC Press, Florida (1983), Vol. 1, pp. 37-50; Gains, N. and Hauser, H. in: *ibid.*, Vol. 1, pp. 67-78; Olson, F. et al (1979), *Bio*

Suitable lipids that can be used in preparing the ULVs to be fused to form the proteoliposomes of the present invention include all phospholipids. The fusogenic ULVs may be composed of one type of phospholipid or a mixture of phospholipids.

Examples of suitable phospholipids include any unsaturated or saturated synthetic phosphatidylcholine; egg or soy phosphatidylcholine as a bulk phospholipid containing saturated phospholipids; DMPC; DSPC; DPPC and hydrogenated egg or soy phosphatidylcholine.

Although it is clear that several different conditions catalyze fusion of ULVs, as, for example, detergents, above the temperature for the main phase transition or the presence of fatty acids in bilayers at a temperature below that for the main phase transition (Kantor, H. L. and Prestegard, J. H. (1978) *Biochem.* 14, 1790–1975), it is not certain what characteristic of bilayers usually accounts for fusion.

As herein used, the main phase transition temperature is the temperature at which a particular phospholipid or mixture of phospholipids change(s) from the gel-crystalline phase to the liquid-crystalline phase.

To become capable of fusion, it is essential that the lipid bilayer have a fusogen incorporated therein. According to the present invention, the fusogenic bilayer is activated when the vesicle is taken to a temperature at or below the phase transition temperature.

The term "fusogen" is used herein to describe any lipophilic molecule that can be included in the phospholipid bilayer which renders the otherwise stable bilayer capable of fusion when any component of the bilayer is at or below the phase transition temperature.

As the fusogen, there may be used any lipophilic molecule which when included in a specific phospholipid or mixture of phospholipids induces fusion of the bilayer with other bilayers and integral membrane proteins. A fusogen can itself be a phospholipid.

Examples of fusogens suitable for use in the present invention include fatty acids, sterols, and phospholipids immiscible with the bulk of the phospholipids of the vesicle.

Examples of fatty acids include myristate (any salt), palmitate, stearate, etc.

Examples of sterols include cholesterol and cholesterol derivatives such as cholesterol esters.

Preferred fatty acids and sterols include myristate, palmitate, stearate and cholesterol.

Preferred immiscible phospholipids include saturated synthetic phosphatidylcholine(s) or hydrogenated egg or soy phosphatidylcholine.

Suitable combinations of phospholipids and fusogens which can be used in preparing the fusogenic unilamellar liposome which will fuse with integral membrane proteins to form proteoliposomes of the present invention include the following:

| Phospholipids | Fusogen |
|---|---|
| dimyristoylphosphatidylcholine (DMPC) | myristate |
| | cholesterol |
| | 1,3 dimyristylphosphatidylcholine |
| | 1,2 distearoyl phosphatidylcholine |
| dipalmitoyl phosphatidylcholine (DPPC) | palmitate |
| | 1,3 dipalmitoyl phosphatidylcholine |
| distearoyl phosphatidylcholine (DSPC) | stearate |
| | 1,3 distearoyl phosphatidylcholine |
| Egg or Soy Phosphatidylcholine | DMPC |
| | DPPC |
| | DSPC |
| | hydrogenated egg or soy phosphatidylcholine |
| Egg or Soy Phosphatidylcholine & DMPC | myristate |
| Egg or Soy Phosphatidylcholine & DPPC | palmitate |
| Egg or Soy Phosphatidylcholine & DSPC | stearate |
| DMPC & gangliosides | myristate |
| DMPC & phosphatidylserine or phosphatidylethanolamine | myristate |

The fusogen is used in an amount sufficient to cause fusion of ULVs with integral membrane proteins at or below the phase transition temperature. The amount of fusogen needed can be determined by monitoring the incorporation of integral membrane proteins into ULVs, after the vesicles have been treated at or below the phase transition temperature for a period of time (generally 5 seconds to 24 hours). The amount of fusogen is greater than 0 but less than 80 mol percent, preferably 1–10 mol percent in relation to bulk phospholipid of the bilayer.

The fusogenic ULVs are prepared by known methods as discussed earlier, including co-sonication; ethanol or ether injection; extrusion procedures; French Press injection; pH adjustment; etc., at temperatures above the phase transition for the phospholipid components of the mixture.

After the fusogenic ULVs are prepared, integral membrane proteins are inserted into the fusogenic ULVs to form proteoliposomes.

The term "integral membrane protein" is used herein to describe any protein derived from a membrane as long as the hydrophobic nature of the protein is within the original membrane.

Essential characteristics of integral membrane proteins include:

1. These proteins are firmly embedded in the phospholipid bilayer of the membrane.
2. Removal of the integral membrane protein requires detergents or other chaotropic agents which disrupt and/or dissolve the membrane.
3. These proteins have a large net hydrophobic nature, i.e., the proteins are not soluble in aqueous solution.
4. These proteins will not remain in solution without the presence of small amphipathic molecules.

Some suitable integral membrane proteins include bacteriorhodopsin, UDP-glucuronyltransferase, cytochrome oxidase, insulin receptor, and the $\beta C_I$ complex. However, all integral membrane proteins are believed to be suitable for the present invention.

Especially preferred integral membrane proteins include bacteriorhodopsin, UDP-glucuronyltransferase, cytochrome oxidase, rhodopsin, erythrocyte membrane proteins: glycophorins, anion transporter (band 3), $CA^{2+}$, $Mg^{2+}$-ATPase Glucose transporter (band 4.5) and the complement receptor (Nelson, D. R. and Robinson, N. C. (1983), "Membrane Proteins: A Summary of Known Structural Information Methods" in *Enzymology* 97, 49: 571–618). Integral membrane proteins can be obtained from all sources, i.e., bacteria, mammal, livestock, erythrocyte membranes, etc.

The integral membrane proteins are inserted (fused) by mixing with fusogenic ULVs at a temperature above or below the phase transition temperature and then lowering or maintaining the temperature of the mixture to a value at or below the phase transition temperature of the fusogenic ULVs for a period of time as discussed below.

According to the present invention, proteoliposomes can be formed by reacting (1) fusogenic ULVs with integral membrane proteins, (2) fusogenic ULVs with fusogenic proteoliposomes and (3) fusogenic proteoliposomes with each other.

In this manner, the ULVs can be enlarged and, accordingly, made more stable for carrying drugs or other substances. The extent of secondary growth of the proteoliposomes can be limited by the availability of fusogenic ULVs in the mixture and the process of secondary growth can be stopped at any time by raising the temperature to above the phase transition of the particular phospholipid mixture of the proteoliposomes and ULVs. The proportion of ULVs, i.e., ULVs converted to proteoliposomes, is readily determined by gradient centrifugation by one skilled in the art. The separation of these two components, ULVs and proteoliposomes by centrifugation or chromatographic procedures, also is readily performed by one skilled in the art.

"Secondary growth" means the fusion of other fusogenic ULVs with the proteoliposome There is no "primary growth", but the primary event is the fusion of integral membrane proteins with fusogenic ULVs.

In a given reaction mixture, fusogenic ULVs can also react with each other to form large ULVs. Further, fusion of ULVs is predominately a binary fusion, but the fusion of clumps of vesicles is not unlikely.

Only two relevant steps of the method for the integration or fusion of integral membrane proteins into fusogenic ULVs and the fusion of fusogenic ULVs with the proteoliposomes or proteoliposomes with each other are required after the components comprising integral membrane protein and fusogenic ULVs are mixed at a temperature above, at, or below the phase transition temperature:

1. Temperature:

The mixture is then brought to or maintained at a temperature at or below the phase transition temperature. Each phospholipid composition will have its own phase transition temperature. Each fusogen will have its own temperature at or below the phase transition at which a maximum rate of fusion occurs. However, fusion events will occur at all temperatures at or below the phase transition temperature until the reaction mixture freezes, which is not necessarily 0° C.

The gel-crystalline phase (i.e., frozen) exists below the phase transition temperature. The liquid crystalline phase (i.e., liquid) exits above the phase transition temperature (neither phase is totally frozen or liquid but rather some degree of that condition).

Phase transitions are determined for each phospholipid by biophysical methods in general such as calorimetric assays, etc. These methods are well documented in the literature.

A suitable temperature range for incorporation of integral membrane protein and fusion with proteoliposomes or proteoliposomes with other proteoliposomes is 0–37° C., although this depends on the phospholipid and fusogen used as mentioned above. For example, the temperature for incorporation is 18° C. for DMPC and myristate, 21° C. for DMPC and cholesterol, and 7–15° C. for egg phosphatidylcholine and DMPC.

2. Time of Fusion Below the Phase Transition Temperature:

The length of time the mixture is allowed to fuse will determine the extent of the reaction; this is from greater than no time to several days. Preferred reaction times are 5–10 seconds to 2 hours. The concentration of ULVs and protein is arbitrary and depends on what is available. There are no constraints of concentration on the reagents for this process. Furthermore, all normal buffers and ionic conditions are tolerated.

The amount of integral membrane protein used is in relation to the phospholipid concentration. A suitable lipid to protein ratio (wt/wt) of 100/1 to 1/10, preferably 20/1 to 1/10.

The process of integration of integral membrane proteins and/or fusion of fusogenic ULVs with proteoliposomes or proteoliposomes with each other depends critically on temperature and the presence of a fusogen in the ULV. No incorporation of integral membrane protein, fusion of fusogenic ULVs with proteoliposomes, or fusion of proteoliposomes with each other occurs, for example, above the phase transition temperature for the fusogenic ULV. Reduction of the temperature of mixtures of integral membrane proteins and fusogenic ULVs to below the phase transition temperature for the lipid results in the two-stage reconstitution process described above. Without a fusogen in the ULV, no incorporation or fusion occurs.

According to the present invention, the medicament comprises a lipid vesicle associated with a drug or other biologically active or physiologically active agent.

The lipid protein vesicle can be associated with the drug or other agent by encapsulation based on passive permeability at or below the phase transition temperature (van Hoogevest, P. et al (1984) *FEBS Lett.* 171, 160–164). Another and preferred method for the encapsulation of drugs and other agents is the extrusion process (Alson, F. et al. (1979), *Biochem. Biophys. Acta* 557, 9–23. A specific application of the extrusion procedure is for the encapsulation of hemoglobin (Gaber, B. P. et al (1983), *FEBS Lett.*, 153, 285–288). Other methods for the preparation of trapped drugs are known to those in the field. Several methods which can be used are freeze thaw, reverse-phase evaporation technique, ether injection methods, extrusion procedures, sonication, etc.

A drug may be present in these vesicles prior to fusion to achieve encapsulation of said drug in the proteoliposome. Alternatively, a small molecular weight drug may b loaded into the fusogenic ULVs and fusogenic proteoliposomes by passive permeability under the conditions necessary for fusion. This permeability is due to pores formed in the phospholipid bilayer by the presence of the fusogens and the gel-crystalline phospholipids (van Hoogevest, P. et al (1984), *FEBS Lett.* 171, 160–164).

Drugs may be included in fusogenic vesicles which are then fused with fusogenic proteoliposomes.

Suitable drugs and other biologically active or physiologically active agents which can be associated with the ULV include antineoplastic agents, enzymes and proteins that are soluble in water and genes (i.e., nucleic acid).

An especially preferred physiologically active agent is hemoglobin with or without 2,3-diphosphoglycerate (1–10 mol/mol ratio hemoglobin to a 2,3-diphosphoglycerate, preferably 1–3 mol/mol). Covalent hemoglobin derivatives and/or thiocyanate hemoglobin adducts can also be used.

A suitable amount of the drug or other biologically or physiologically active agent is 1–30 gm/dl, preferably 15 gm/dl relative to a solution comprising 50% proteoliposomes by volume.

The medicament can be administered by intravenous injection.

The doses can readily be determined by one of ordinary skill in the art.

An especially preferred medicament is one wherein the proteoliposome is a phospholipid ULV having erythrocyte integral membrane proteins. An erythrocyte integral membrane protein is any membrane protein isolated from salt washed erythrocyte membranes.

The above-described medicaments can be used in treating numerous medical conditions including cancer, genetic diseases, and blood loss.

The present invention will now be described in detail by reference to specific examples demonstrating conditions under which different integral membrane proteins can be inserted rapidly into preformed unilamellar vesicles of DMPC in accordance with this invention. It is to be understood that the examples given below are for illustration only and the present invention is not intended to be limited thereto.

EXAMPLES

Example 1

Preparation of Proteoliposomes from DMPC and Myristate 63 mg of DMPC and any concentration of myistate (i.e., >0 to 4mg) were hydrated and 9 ml of any suitable buffer (e.g., tris-HCl, pH 7.5, 100 mmol KCl) at 30° C. The material was sonicated for 30 minutes with a ⅜" horn at 30% of maximum power. The output was pulsed so that power was delivered for 60 percent of the total time of sonication. The samples of the vesicles appeared clear at the end of sonication. The vesicles were centrifuged at 140,000 xg for 30 minutes at 37° C. to remove titanium particles and any multilamellar vesicles which may have remained at the end of sonication.

In the practice of the invention, it is preferred to use ultrasonic energy as a means for preparing vesicles of lipid containing a fusogen. In this case, myristate.

The fusion of integral membrane protein (i.e., bacteriorhodopsin) and the fusogenic ULV was accomplished by mixing these two components. (For example, 250 μg of bateriorhodopsin and 3 mg of fusogenic UVLs of DMPC containing myristate.)

The mixing may be performed at any temperature above or at or below the phase transition temperature of the fusogenic DMPC myristrate vesicle (23° C.).

In the first case, the integral membrane protein does not fuse with (incorporate into) fusogenic ULVs until the temperature is lowered to at or below 23° C. The maximum rate of this fusion event (incorporation of integral membrane protein) and the other fusion events (vesicle to vesicle or proteoliposome or proteoliposome to proteoliposome) occurs at 18° C. This process may be allowed to continue as long as the mixture is at or below 23° C. The longer the time the mixture is treated under fusing conditions, the larger the proteoliposomes grow and the greater the lipid to protein ratio.

In the second case, precooled components are mixed at any temperature at or below the phase transition temperature for DMPC (23° C.) and the incorporation or fusion of the integral membrane protein is spontaneous. After the primary event, the secondary growth of the proteoliposome is the same as described in the first case.

In both instances, a second addition of integral membrane protein may be added to the reacting mixtures. This solution of integral membrane protein can be at any acceptable temperature where the immediate incorporation of the added integral membrane protein occurs. This step can be repeated until no further integral membrane protein is incorporated into the vesicles. This results in a decrease of the final lipid/protein ratio of the proteoliposomes.

Alternatively, the addition of more fusogenic ULV of DMPC containing myristate can be performed. This type of addition results in an increase of the lipid/protein ratio and size of the proteoliposome. Lipid vesicles, proteoliposomes and proteins can be separated from each other by centrifugation on glycerol gradients.

Example 2

Preparation of Proteoliposomes from DMPC and Cholesterol 60 mg of DMPC and any concentration of cholesterol (<0 to 30 mg) were hydrated in 9 ml of any suitable buffer, as described in Example 1, at 37° C. Vesicles (fusogen ULV) were prepared as described in Example 1. The fusion of a mixture of integral membrane proteins and fusogenic ULV of DMPC containing cholesterol followed the procedure in Example 1 with two exceptions. In the first exception, the temperature of maximum fusion (incorporation and vesicle to vesicle fusion) occurred at 21° C. In the second exception, the use of low temperature (i.e., 5° C.) caused only incorporation, (i.e., fusion of integral membrane protein with fusogenic ULVs). The secondary phase of fusion, growth of the proteoliposome by fusion with other fusogenic ULVs or fusogenic proteoliposomes, did not begin until the temperature was raised closer to the phase transition temperature (i.e., 21° C.).

Example 3

Preparation of Proteoliposomes from Egg Phosphaticdyl Choline, DMPC, DPPC, DSPC and myristrate, palmitate, or stearate 21 mg of egg phosphatidylcholine containing 9 mg of a saturated phosphatidylcholine; DMPC, DPPC and DSPC, and (>0–1 mg) saturated fatty acid; myristate, palmitate or stearate were hydrated in 9 ml of any suitable buffer, as described in Example 1, at 37°, 47° or 60° C., respectively. Vesicles (fusogenic ULVs) were prepared as described in Example 1 except for the indicated temperatures which were maintained during sonication. Fusion occurred at temperatures at or below the phase transition temperature for the saturated phospholipid added, i.e., DMPC≦23° C., DPPC≦45° C. and DSPC≦56° C. Otherwise, the fusion of the mixture of integral membrane protein and fusogenic ULVs comprising egg phosphatidylcholine containing saturated phosphatidylcholine and fatty acid, followed the procedure in Example 1. Optionally, cholesterol (6 mg) could be added to these vesicles.

Example 4

Preparation of Proteoliposomes from DMPC, bovine phosphatidyl serine and myristate 42 mg of DMPC containing 21 mg of bovine phosphatidylserine and 2.4 mg of myristate were hydrated in 9 ml of any suitable buffer, as described in Example 1, at 30° C. Otherwise, the procedure as described in Example 1 was followed to give proteoliposomes.

What is claimed is:
1. A process for the preparation of fusogenic proteoliposomes comprising:
 (a) mixing a fusogen with a lipid component used to form unilamellar lipid vesicles to thereby form fusogenic unilamellar lipid vesicles;
 (b) mixing said fusogenic unilamellar lipid vesicles with integral membrane proteins; and
 (c) lowering the temperature of the mixture of fusogenic unilamellar lipid vesicles and integral membrane proteins to at or below the phase transition temperature of the fusogenic unilamellar lipid vesicles to thereby form fusogenic proteoliposomes.

2. The process of claim 1, wherein said integral membrane proteins and said fusogenic unilamellar lipid vesicles are present in an amount sufficient to form said fusogenic proteoliposomes of about 0.1 to 10 μ in size.

3. The process of claim 1, wherein said lipid component used to form said unilamellar lipid vesicles is a phospholipid or a mixture of one or more phospholipids.

4. The process of claim 1, wherein said fusogen is a fatty acid, sterol or phospholipid which when included in a phospholipid bilayer renders the bilayer capable of fusion with integral membrane proteins when any component of the bilayer is at or below the phase transition temperature.

5. The process of claim 4, wherein said fusogen is at least one member selected from the group consisting of myristate, palmitate, stearate, cholesterol, saturated phosphatidylcholine dimyristoylphosphatidylcholine, distearoyl phosphatidylcholine, dipalmitoyl phosphatidylcholine hydrogenated egg phosphatidylcholine and hydrogenated soy phosphatidylcholine.

6. The process of claim 3, wherein said phospholipid is egg or soy phosphatidylcholine or any unsaturated or saturated synthetic phosphatidylcholine.

7. The process of claim 1, wherein said integral membrane protein is bacteriorhodopsin, UDP-glucuronyltransferase, cytochrome oxidase, insulin receptor or $\beta C_1$ complex.

8. The process of claim 1, wherein said integral membrane protein is used in an amount such that the lipid to protein ratio (wt/wt) is 100/1 to 1/10.

9. The process of claim 8, wherein the lipid to protein ratio (wt/wt) is 20/1 to 1/10.

10. The process of claim 1, wherein the unilamellar lipid vesicles are phospholipid vesicles and the integral membrane proteins are erythrocyte integral membrane proteins.

* * * * *